(12) United States Patent
Annerl

(10) Patent No.: US 9,623,042 B2
(45) Date of Patent: Apr. 18, 2017

(54) COMBINATION PREPARATION FOR IMPROVING SPERM QUALITY

(75) Inventor: Brigitte Annerl, Vienna (AT)

(73) Assignee: Fapa Vital Anstalt, Gamprin-Bendern (LI)

( * ) Notice: Subject to any disclaimer, the term of this patent is extended or adjusted under 35 U.S.C. 154(b) by 2315 days.

(21) Appl. No.: 13/575,027

(22) PCT Filed: Feb. 5, 2007

(86) PCT No.: PCT/AT2007/000055
§ 371 (c)(1),
(2), (4) Date: Nov. 26, 2012

(87) PCT Pub. No.: WO2007/087667
PCT Pub. Date: Aug. 9, 2007

(65) Prior Publication Data
US 2013/0295068 A1    Nov. 7, 2013

(30) Foreign Application Priority Data
Feb. 3, 2006 (AT) .................... A 172/2006

(51) Int. Cl.
| | | |
|---|---|---|
| *A61K 31/197* | (2006.01) | |
| *A61K 31/714* | (2006.01) | |
| *A61K 31/122* | (2006.01) | |
| *A61K 31/205* | (2006.01) | |
| *A61K 31/355* | (2006.01) | |
| *A61K 31/519* | (2006.01) | |
| *A61K 33/04* | (2006.01) | |
| *A61K 33/30* | (2006.01) | |
| *A61K 38/06* | (2006.01) | |
| *A61K 45/06* | (2006.01) | |
| *A61K 31/198* | (2006.01) | |
| *A61K 31/375* | (2006.01) | |
| *A61K 31/385* | (2006.01) | |
| *A61K 31/4188* | (2006.01) | |
| *A61K 31/51* | (2006.01) | |
| *A61K 36/258* | (2006.01) | |

(52) U.S. Cl.
CPC .......... *A61K 31/714* (2013.01); *A61K 31/122* (2013.01); *A61K 31/198* (2013.01); *A61K 31/205* (2013.01); *A61K 31/355* (2013.01); *A61K 31/375* (2013.01); *A61K 31/385* (2013.01); *A61K 31/4188* (2013.01); *A61K 31/51* (2013.01); *A61K 31/519* (2013.01); *A61K 33/04* (2013.01); *A61K 33/30* (2013.01); *A61K 36/258* (2013.01); *A61K 38/063* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 6,338,862 B1 | 1/2002 | Niazi | |
| 6,368,617 B1 | 4/2002 | Hastings et al. | |
| 2001/0031744 A1* | 10/2001 | Kosbab | 514/54 |
| 2002/0122834 A1 | 9/2002 | Trant | |
| 2003/0224070 A1 | 12/2003 | Sweazy et al. | |
| 2005/0181044 A1 | 8/2005 | Romero | |
| 2009/0081177 A1* | 3/2009 | Tremellen | 424/94.1 |

FOREIGN PATENT DOCUMENTS

| | | | |
|---|---|---|---|
| DE | 10036798 A1 | 2/2002 | |
| DE | 10036799 A1 | 2/2002 | |
| DE | 10158498 A1 | 7/2003 | |
| EP | 0799578 B1 | 7/2002 | |
| EP | 1714658 A1 | 10/2006 | |
| WO | 9927925 A1 | 6/1999 | |
| WO | 9417799 A1 | 8/1999 | |
| WO | WO0053176 * | 9/2000 | A61K 31/385 |
| WO | WO0203974 A2 | 1/2002 | |
| WO | 0212882 A2 | 2/2002 | |
| WO | 03026438 A1 | 4/2003 | |
| WO | WO03032751 A1 | 4/2003 | |
| WO | WO03086080 A1 | 10/2003 | |
| WO | WO2007003007 A1 | 1/2007 | |

OTHER PUBLICATIONS

Nutrition Facts, Maca Powder, retrieved from the Internet Nov. 17, 2014: http://nutritiondata.self.com/facts/custom/2193874/0?print=true.*
Agarwal et al., Carnitines and male fertility, RBMOnline, vol. 8, No. 4, 2004, pp. 376-384.*
Amino Acid Calculation for Garlic, retrieved from the internet, May 26, 2016: www.healthaliciousness.com/nutritionfacts/amino-acid-calculator.php?o=11215&t=11215&h=11215&s=&e=&r=.*
Sinclair, Steven, Male Infertility: Nutritional and Environmental Considerations, Alternative Medicine Review, 2000, pp. 28-38, vol. 5, No. 1, Thorne Research, Inc., Sandpoint, United States.
Shah, Priya F., "Male Infertility and Glutathione", Men's Issues, SelfGrowth.com: The Online Self Improvement Encyclopedia, www.selfgrowth.com, Feb. 16, 2004.
Sheweita, Salah A. et al., "Mechanisms of Male Infertility: Role of Antioxidants", Current Drug Metabolism, 2005, 6, pp. 495-501.
Rosick, Ed, "Increasing Male Fertility and Longevity", LE Magazine, http://www.lef.org/magazine/mag2003/jul2003_report_male_01.htm, Jul. 2003.
Irvine, D. Stewart, "Glutathione as a treatment for male infertility", Reviews of Reproduction, (1996) 1, pp. 6-12.
Meletis, Chris D. et al., "Natural Ways to Enhance Male Fertility", Alternative & Complementary Therapies, Feb. 2004, pp. 22-27.

(Continued)

*Primary Examiner* — Thane Underdahl
*Assistant Examiner* — Yvonne Pyla
(74) *Attorney, Agent, or Firm* — Medler Ferro Woodhouse & Mills PLLC

(57) ABSTRACT

The invention relates to a combination preparation for improving the sperm quality and capacitation of a male individual. Said combination preparation comprises effective amounts of L-carnitine, coenzyme $Q_{10}$, at least one vitamin E, particularly α-tocopherol, at least one source of zinc, especially zinc sulfate or zinc chloride, at least one source of vitamin B, particularly folic acid, at least one source of selenium, glutathione, and arginine or salts or derivatives thereof as active substances.

6 Claims, No Drawings

(56) References Cited

OTHER PUBLICATIONS

Wong, W.Y. et al., "Effects of folic acid and zinc sulphate on male factor subfertility: a double-blind, randomized, placebo-controlled trial", Fertility and Sterility, Mar. 2002, vol. 77. No. 3, pp. 491-498, Published by Elsevier Science Inc.

Oishi, Kimihiko et al., "Male infertility due to germ cell apoptosis in mice lacking the thiamine carrier, Tht1. A new insight into the critical role of thiamine in spermatogenesis", Developmental Biology, 2004, 266 (2), pp. 299-309.

Dakshinamurti, K., "Biotin—a regulator of gene expression", The Journal of Nutritional Biochemistry, Jul. 2005, 16 (7), S. 419-23.

Souci, Der Kleine et al., Lebensmitteltabelle für die Praxis, 3rd edition, Wiss. Stuttgart, Germany, 2004, pp. 15-16, 243.

Belitz, H. D. and Grosch, W. Lehrbuch der Lebensmittelchemie, 4th edition, Germany, 1992, p. 19.

Schmidt, E. and Schmidt, N, Leitfaden Mikronährstoffe: orthomolekulare Prävention und Therapie, Elsevier, Urban & Fischer, 2004, p. 558.

\* cited by examiner

COMBINATION PREPARATION FOR IMPROVING SPERM QUALITY

CROSS-REFERENCE TO RELATED APPLICATIONS

This application is a national phase entry under 35 U.S.C. §371 of PCT/AT2007/000055 filed on Feb. 5, 2007, which claims priority to Austrian Patent Application A 172/2006 filed on Feb. 3, 2006, the entirety of each of which is incorporated by this reference.

FIELD OF THE INVENTION

The invention relates to a combination preparation, as well as to a method for the production of a combination preparation for treatment of restricted fertility in men.

DESCRIPTION OF THE RELATED ART

Fertility treatment of couples who are unable to conceive has been gaining importance in practical medicine in recent years. In the meantime, infertility affects one in six couples who wish to have children. The cause for inability to conceive can lie both with the woman and with the man, but the male factor has been gaining importance in recent years. In contrast to women, for whom a number of therapeutic possibilities is available, the options for improving the single and decisive factor, namely the sperm quality, are very limited for men.

Both the quality and the quantity of the male sperm are influenced by numerous factors. Various environmental stresses (pollutants, heavy metals, etc.), stressful lifestyle factors (such as nicotine, alcohol, etc.) and changed circumstances of life (marked stress) nowadays place a burden on sperm development as well as on motility, appearance and number of sperm. Sperm production is a very complicated and biologically effortful process, which occurs over a period of several weeks and can easily be influenced in negative manner. Within the scope of sperm cell maturation, the body needs special ancillary substances during the different development steps. These include various amino acids, trace elements, vitamins and substances similar to vitamins. Only with these special vital substances do optimal prerequisites for normal and healthy sperm formation exist. A deficiency of these substances can easily occur as the result of certain life circumstances and an incorrect lifestyle, and this is often not noticed by those affected. For this reason, a regular supply of these substances, in a sufficient amount, is absolutely necessary.

Many individual substances important for the progression of sperm cell maturation have already been investigated and described scientifically. The efficacy of each individual vital substance is sufficiently known.

The individual components and their methods of effect are all known, at present, in separate manner. In the following, an overview of the individual active substances is given:

L-carnitine [6645-46-1]: L-carnitine is a substance produced by the body itself, which serves as an energy substrate for the sperm. L-carnitine can bring about an improvement in the sperm motility and the sperm count.

L-arginine [74-79-3]: L-arginine is an amino acid that is needed by the body in large amounts and has led, in studies, to a significant improvement in sperm count and sperm motility.

Coenzyme $Q_{10}$ [303-98-0]: Coenzyme $Q_{10}$, ubiquinone, can lead to an improvement in the fertilization rate, an increase in sperm cell count, and an improvement in sperm motility.

Vitamin E, particularly α-tocopherol [59-02-9]: Vitamin E can improve sperm motility and promotes the ability of the sperm cell to unite with the ovum cell.

Zinc: Zinc is a trace element necessary to life, and on the one hand acts as an antioxidant, i.e. as a substance that binds free radicals or prevents their formation; furthermore, zinc brings about an improvement in sperm cell density, an increase in the number of quickly moving sperm, and an increase in the testosterone level that is important for sperm cell maturation, by means of its involvement in numerous biochemical processes in the body.

Folic acid [75708-92-8]: Folic acid is absolutely necessary for cell growth, cell division (blood formation) as well as for nerve metabolism, and is involved in the protection of the cardiovascular system. The positive effect of this vitamin on sperm quality has already been known for a long time; it has been studied in detail and is recommended for support.

Glutathione [70-18-8] and selenium: Glutathione and selenium are highly effective radical scavengers and can clearly improve the motility of the sperm cells.

Some preparations for improving sperm quality in men are also known from the state of the art, in which preparations some of these active substances are combined with one another.

For example, in WO 02/003974, a preparation for improving sperm quality is described, which is based on a combination of folic acid with zinc sulfate.

Furthermore, in U.S. Pat. No. 6,338,862, a preparation for correcting erectile dysfunction is described, which combines L-arginine, *ginseng*, and various vitamins of the B group.

Up to the present, however, it has been extremely difficult and, in the opinion of many, impossible to achieve significant improvement in fertility by means of treatment with medications, although this has often been propagated and asserted.

BRIEF SUMMARY OF THE INVENTION

It is therefore the task of the present invention to create an effective preparation for improving sperm quality in men, among other things.

This task is accomplished by means of the characteristics of the invention.

The individual substances combined in the combination preparation and carefully selected have proven themselves in terms of their effectiveness for improving sperm quality, and have already been tested.

In studies, the surprising effect of the new combination preparation was shown; it greatly exceeds the total of the individual effects to be expected, and also far exceeds the efficacy of all the compositions that were available until now. By means of administration of the combination preparation according to the invention, it was possible to achieve a clear improvement in sperm quality, up to a completely normal spermiogram. Such treatment results have not become known before now, and the surprising level of efficacy is also extremely advantageous for the patients affected. All fertility-relevant parameters of the spermiogram, such as density, motility, and morphology of the sperm were significantly increased.

As the literature shows, and as was confirmed by comparison tests, none of the individual substances was able to achieve comparable results, which makes it clear that only the special combination of the substances used leads to the desired result.

In this connection, the advantageous effect of arginine and the synergistic effects brought about by arginine should be particularly pointed out, as will be explained in detail below.

Advantageous further developments of the invention are presented in the dependent claims.

The advantageous characteristics of invention describe a particularly effective composition of the combination preparation. By means of such a composition, the interactions of the individual substances with one another are optimized, and the synergy effects are additionally reinforced.

The characteristics of the invention additionally reinforce the effect, where it is advantageous if the concentrations of the invention are adhered to. Because of the great antioxidant capabilities and the known major role of free radicals within the scope of sperm cell maturation, the administration of alpha-lipoic acid is very advantageous in the case of a poor spermiogram. This was already successfully tested clinically in an administration observation. Furthermore, it is known that alpha-lipoic acid raises the glutathione level, which is very important.

The characteristics of the invention bring about a further effect of increasing the action, where it is advantageous if the concentrations are adhered to. N-acetylcysteine (NAC) is a substance that is very important for sufficient glutathione production. The advantageous and surprisingly strong synergistic interplay between glutathione, NAC, and alpha-lipoic acid contributes to a further improvement in sperm quality.

Both in animal experiments and in humans, the administration of Vitamin C, according to the characteristics of the invention, proves to be extremely beneficial for improving sperm quality. Vitamin C significantly reduces lipid oxidation in the testicles, which is harmful to sperm production, and thereby leads to an improvement in sperm quality in the sense of an increase in sperm cell density and an increase in the testosterone level.

The effect of the combination preparation can also be further increased by providing additional characteristics according to the invention.

DETAILED DESCRIPTION OF THE INVENTION

In one study, 66 patients with poor sperm quality were studied. By means of the administration of *ginseng* extract, an increase in sperm cell concentration, motility, and an increase in the testosterone level came about. The addition of *ginseng* also brought about further combinatory effects, particularly with regard to the motility of the sperm cells.

Both in animal experiments and in humans, the administration of Vitamin B12 proved to be an excellent possibility for improving both the sperm cell concentration and the motility.

The dependence of spermiogenesis on thiamine is a new recognition. In animal experiments, it was discovered that test subjects with a thiamine deficiency demonstrate deficits in spermiogenesis in comparison with the control group, and therefore are fertile only with great restrictions. In addition, a negative influence of the thiamine deficiency on the hormone metabolism is suspected. The addition of thiamine also demonstrated surprising increases in efficacy as compared with the known individual substance. The same also holds true for biotin.

A particularly advantageous example of a highly effective combination preparation, the efficacy of which was also proven and confirmed by clinical studies, is described in the characteristics of the invention. This preparation consists of the stated active substances, where the desired surprising effects already occur, in advantageous manner, from the relatively small number of combined active substances.

Furthermore, it is the task of the invention to provide an advantageous use of the combination preparation for the production of a medication.

This task is accomplished by means of the characteristics of the invention, in which the combination preparation is used as an active medication for improving sperm quality or for treatment of restricted fertility. Furthermore, the combination preparation can be used for treatment of sub-fertility of a male individual, particularly a human being, for treatment or optimization of borderline normozoospermia, for treatment of asthenozoospermia, oligozoospermia, teratozoospermia, oligo-astheno-terato-zoospermia, particularly OAT I, OAT II, and/or OAT III, cryptozoospermia, parvisemia and/or for improving impaired capacitation capability.

In this connection, it is particularly advantageous to provide the characteristics of the invention, thereby increasing the efficacy.

By means of the characteristics of the invention, an effective dosage is specified, which can be tolerated by the body, for one thing, and demonstrates the active effects described above, for another thing.

In the meantime, infertility affects one in six couples wishing to conceive. In the meantime, we are beginning to understand the pathologies both on the biochemical level and on the cellular level, which then cause the production of defective sperm cells, as a further consequence.

ROS (reactive oxygen species) are reaction products that attack the lipids of the sperm cell membrane and thereby initiate a peroxidation cascade. As a result, the spermatozoa lose their ability to move; the acrosome reaction and fusion between sperm cell and ovum cell is no longer possible. ROS hinder mitochondria function and negatively influence the synthesis of DNA, RNA, and the formation of proteins. At this point, two substances of the combination preparation already come into use.

L-carnitine and coenzyme $Q_{10}$ act on the cellular level, in that they are decisively involved in the energy metabolism of the mitochondria in the cells.

L-arginine, an important amino acid, represents a fundamental building block for protein biosynthesis. Only by means of a sufficient supply of these substances in the body can the functions mentioned above be guaranteed.

Arginine, in the combination preparation according to the invention, brings about an effect of increasing sperm quality and promoting fertility, in three ways. Primarily, it brings about an independent positive effect on sperm motility and the number of sperm. Secondarily, the unusually strong effect of arginine on the regulation of nitrogen monoxide brings about optimization of the metabolism milieu as a starting situation for an improved effect of all the other ingredients. Arginine therefore has an advantageous influence on the efficacy of the other ingredients of the combination preparation. The potent reduction of the oxidative stress gives the functionally active components of the preparation a significantly improved starting situation and thereby clearly strengthens their effect on mobility and motility. This is a reason why the combination of the individual substances brings about an improvement in the influence on motility and sperm count, which goes beyond the effect of the individual substances. As it was possible to show in our own study as cited, the effect is surprisingly improved in such a manner that at the end of the study, nine normal spermiograms (29%) were obtained. The third mechanism of effect of arginine is based on the clear improvement in the capacitation capability of the sperm, namely the preparation for and the penetration itself of the sperm into the ovum cell.

This property of L-arginine, in combination with the other ingredients, particularly with Vitamin E, zinc, and glutathione, also is the reason for the surprising development that it was possible to observe four pregnancies already within the study and six pregnancies barely after the end of the study.

Glutathione plays a significant role in antioxidant defense of sperm cell epithelia, in the epididymis, and, in general, in the ejaculate. This highly effective antioxidant can maintain the functionality of the sperm cells particularly well only in combination with selenium. Both the testicles and the epididymis, and therefore spermatogenesis, are dependent on the defense mechanisms of the combination of glutathione and selenium. This takes place, among other things, by way of the enzymes superoxide dismutase (SOD) and glutathione peroxidase, which can prevent damaging lipid oxidation. Other foreign and harmful substances (environmental toxins) are deactivated by the enzyme glutathione-S-transferase.

These protective mechanisms as described function only under specific conditions, to a limited extent, and also only in combination with and with the support of other antioxidants.

These include zinc, which is involved in almost all important biochemical processes of the body.

In addition, a combination of the antioxidant substances Vitamin E, supplemented with folic acid from the Vitamin B complex, is required. These two vitamins play a supportive role in spermiogenesis and are absolutely necessary in this combination.

Thus, the surprising efficacy of this preparation consists of the synergistic interaction of the individual substances.

In the tables below, a combination preparation according to the invention, which develops the advantageous effects, is described as an example.

TABLE 1

| Ingredients | Amount of active substances per capsule | Wt.-% with reference to the total amount of active substances (Example) | Recommended amount [mg] per day (range) | Recommended amount [mg] per day (Example) |
| --- | --- | --- | --- | --- |
| L-carnitine | 220 mg | 46.5 | 100-5000 | 440 |
| L-arginine | 125 mg | 26.4 | 100-5000 | 250 |
| Coenzyme $Q_{10}$ | 7.5 mg | 1.59 | 5-250 | 15 |
| Vitamin E | 60 mg | 12.7 | 50-1000 | 120 |
| Zinc | 20 mg | 4.23 | 5-100 | 40 |
| Folic acid | 0.4 mg | 0.085 | 0.1-1 | 0.8 |
| Glutathione | 40 mg | 8.46 | 10-1000 | 80 |
| Selenium | 0.03 mg | 0.0063 | 0.01-1 | 0.06 |
| Active substances in total | 472.93 mg | 100.00% | | |

TABLE 2

| Ingredients | Amount of active substances taken in per day | Wt.-% with reference to the total weight of the combination preparation including fillers (Example) per capsule |
| --- | --- | --- |
| L-carnitine | 440 mg | 25.9 |
| L-arginine | 250 mg | 14.7 |
| Coenzyme $Q_{10}$ | 15 mg | 0.9 |
| Vitamin E | 120 mg | 7.1 |
| Zinc | 40 mg | 2.4 |
| Folic acid | 400 µg | 0.0475 |
| Glutathione | 80 mg | 4.7 |
| Selenium | 60 µg | 0.0035 |
| Total of active substances | | 55.7506 |
| Remainder fillers (not actively effective) | | approx. 44.2 |
| Total as a whole | | 100.0000 |

In Table 1, the composition of a particularly effective combination preparation, the efficacy of which has been confirmed clinically, is described in detail. The combination preparation is present in capsule form, where the active water-soluble and fat-soluble substances are present in the interior of the capsule as a granulate.

According to this example, one capsule contains 472.93 mg of active substances. According to Table 2, this corresponds to an amount of approx. 56 wt.-% with reference to the total weight of the capsule contents. The remaining 44% are fillers, for example starch, which are advantageous for technical processability of the granulate. However, these technical fillers have no efficacy and no positive effects on sperm quality, and are accordingly not active substances in the sense of those mentioned above.

In Table 1, the percentage composition or the ratio of the active substances to one another is furthermore described in wt.-%. Here, glutathione has the decisive influence on the efficacy of the preparation, because the combinatory or synergistic effects are reinforced and additionally cranked up by glutathione.

In Table 1, the ranges of the recommended daily doses and the recommended dosage when taking two capsules a day are furthermore indicated in the last two columns.

The combination preparations according to the invention can particularly be formulations and/or compositions that are directed at and/or suitable for oral administration to a male individual of a mammalian species, comprising but not restricted to pharmaceutical, dietetic or veterinary formulations or compositions and/or nutritional supplements. The combination preparation is therefore suitable both for human nutrition and for animal nutrition.

The term "a source for" relates to a compound that is suitable for administration, particularly oral administration, to a male individual of a mammalian species, and which makes the desired substance available and/or biologically accessible to the individual, in each instance, in the case of such administration.

Thus, "a source for Vitamin B, particularly folic acid" is to be understood to mean a substance that leads to elevated levels of folic acid in the body or in at least a part thereof, comprising but not restricted to a biological fluid such as blood, plasma and/or semen. Sources of folic acid are, for example, folic acid and its salts, folate compounds, or, optionally, suitable analogs, precursors and/or metabolites of folic acid or folate compounds or any suitable combination thereof. The source(s) of folic acid can be present in suitable reduced or oxidized form, as is also clear to a person of average skill in the art. Some specific examples of suitable sources of folic acid comprise monoglutamate and polyglutamate forms of folic acid, salts and/or esters of folic acid and/or methylated derivatives of folic acid, for example folinic acid or 5-methyltetrahydrofolic acid or any desired combination thereof. The reduced monoglutamate form can also be used.

The term "a source for zinc" refers to a compound that is suitable for administration, particularly oral administration, to a male individual of a mammalian species and which makes zinc available or biologically available after administration, particularly in the form of $Zn^{2+}$ ions. Suitable examples of such biologically available sources of zinc comprise biologically available zinc salts with inorganic ions such as chloride, carbonate, and sulfate, but also zinc salts with organic anions such as lactate, gluconate, fructose phosphates, orotates, citrates, malates, pyruvates, etc., and zinc complexes with an organic molecule such as an amino acid, or a divalent or trivalent compound or any suitable combination thereof.

The same holds true for the further substances, which can also be present in any form, either as an organic or inorganic salt or a derivative, which makes the active substance biologically available to the body.

The term "in effective amounts" should be understood to mean those amounts that are knowingly and intentionally contained, in therapeutically sufficient amounts. Slight contaminants, particularly those without a therapeutic effect, are not included therein.

A study was conducted to document the advantageous and surprising effects. A total of 40 men who had been trying to have children for many years and had at least two pathological spermiograms in their anamnesis were included in this study. These patients received the combination preparation according to the invention over a period of a total of three months. The daily dose was two capsules, corresponding to an amount of active substances as evident from the last column of Table 1. After a period of administration of three months, a control spermiogram was conducted. Up to the present, it has been possible to evaluate 18 patients.

The study yielded the following clear results:

The ejaculation volume, with reference to the entire group, increased from 53.1 ml to 66.5 ml, on average. This corresponds to an increase of 13.4 ml, in total, and an average increase in the ejaculation volume of 0.74 ml per patient. An increase was found in 14 of 18 patients.

The sperm density increased from 60.7 million/ml to 94.5 million/ml. This corresponds to a difference of 33.8 million/ml. An increase in the sperm count was recorded for 15 of 18 patients. On average, the sperm count per milliliter therefore increased by 18.8 million in every patient. In some individual cases, an increase in sperm count by up to 620% came about.

By means of the use of the combination preparation, the number of significant, quickly moving sperm cells increased from a total of 17.1% to 34.5%. It was therefore more than doubled. Here, too, this improvement occurred in 15 of 18 cases. The total motility, in other words quickly moving and slowly moving, increased from a total of 62.2% to 88.7%. This corresponds to an increase in motile sperm cells by just under 15% per test subject.

It was possible to more than double the number of morphologically normal sperm cells, with reference to the total group. The increase was 103%.

In almost all the study participants who have been evaluated up to the present, an improvement occurred in all the relevant parameters. In 7 of 18, the pathologies that existed in the spermiogram for many years normalized to such an extent that the diagnosis was now normozoospermia. Up to the present date, three pregnancies also occurred within the study.

The combination preparation should be taken twice a day in the form of one capsule, with a small amount of fluid or at a meal. The minimum period of administration is three months, in order to be able to optimize every stage of sperm formation. However, the combination preparation can and should continue to be used until a pregnancy occurs.

The combination preparation is present as an encapsulated granulate, where the capsule material is produced entirely from plant substances, particularly cellulose. Thus, the preparation is also particularly well suited for vegetarians.

In Table 3, further active substances that can optionally be used are described, which additionally synergistically reinforce the effects, if at least one of them is additionally used.

TABLE 3

| Other possible ingredients | Recommended amount [mg] per day [range] | Recommended amount [mg] per day (Example) |
| --- | --- | --- |
| Vitamin C (ascorbic acid) | 100-1000 | 500 |
| Vitamin $B_{12}$ (methylcobalamin) | 0.1-5 | 1.25 |
| Vitamin $B_1$ (thiamine) | 10-500 | 100 |
| Vitamin B7 (biotin) | 0.5-10 | 2.5 |
| Ginseng | 500-2000 | 1000 |
| α-lipoic acid | 100-1000 | 600 |
| N-acetylcysteine | 100-1000 | 600 |

The invention claimed is:

1. A sperm quality improving composition, comprising:
  an effective amount of a plurality of active ingredients for a male patient suffering from low sperm quality, the plurality of active ingredients consisting of:
  L-carnitine or salts thereof;
  coenzyme $Q_{10}$ or salts thereof;
  at least one vitamin E or salts thereof;
  at least one source of zinc or salts thereof;
  folic acid or salts thereof;
  at least one source of selenium or salts thereof;
  glutathione or salts thereof; and
  L-arginine or salts thereof, wherein these active ingredients are in amounts to improve sperm quality.

2. The composition of claim 1, wherein the at least one vitamin E comprises α-tocopherol or salts thereof.

3. The composition of claim 1, wherein the at least one source of zinc comprises at least one of zinc sulfate, zinc chloride or salts thereof.

4. The composition of claim 1, comprising:
  25 to 65% by weight of a total weight of the plurality of active ingredients of L-carnitine or salts thereof;
  0.5 to 11% by weight of coenzyme $Q_{10}$ or salts thereof;
  4 to 30% by weight of a total weight of the plurality of active ingredients of a vitamin E or salts thereof;
  0.5 to 20% by weight of a total weight of the plurality of active ingredients of a source of zinc or salts thereof;
  0.01 to 1% by weight of a total weight of the plurality of active ingredients of folic acid or salts thereof;
  0.001 to 0.1% by weight of a total weight of the plurality of active ingredients of a source of selenium or salts thereof;

1 to 25% by weight of a total weight of the plurality of active ingredients of glutathione or salts thereof; and 15 to 45% by weight of a total weight of the plurality of active ingredients of L-arginine or salts thereof.

5. The composition of claim 1, wherein the plurality of active ingredients consist of:

approximately 46 to 47% by weight of the total weight of the plurality of active ingredients of L-carnitine;

approximately 1.5 to 1.6% by weight of the total weight of the plurality of active ingredients of coenzyme $Q_{10}$;

approximately 12 to 13% by weight of the total weight of the plurality of active ingredients of a vitamin E;

approximately 4 to 5% by weight of the total weight of the plurality of active ingredients of a source of zinc;

approximately 0.08 to 0.09% by weight of the total weight of the plurality of active ingredients of folic acid;

approximately 0.08 to 0.09% by weight of the total weight of the plurality of active ingredients of a source of selenium;

approximately 8 to 9% by weight of the total weight of the plurality of active ingredients of glutathione; and approximately 26 to 27% by weight of the total weight of the plurality of active ingredients of L-arginine.

6. The composition of claim 1, wherein the composition is used to increase at least one sperm characteristic selected from the group consisting of density, motility, morphology, concentration, quantity and capacitation capability.

* * * * *